United States Patent [19]

Atwell

[11] 4,445,390
[45] May 1, 1984

[54] SAMPLING TUBE AND APPARATUS

[75] Inventor: William L. Atwell, St. Joseph, Mich.

[73] Assignee: Leco Corporation, St. Joseph, Mich.

[21] Appl. No.: 446,186

[22] Filed: Dec. 2, 1982

[51] Int. Cl.³ .......................... G01N 1/12; G01N 1/24
[52] U.S. Cl. ............................... 73/864.52; 73/863.21; 73/864.82
[58] Field of Search ......... 73/DIG. 9, 864.52, 863.21, 73/864.82

[56] References Cited

U.S. PATENT DOCUMENTS

| 3,315,529 | 4/1967 | Feichtinger | 73/DIG. 9 |
| 3,672,227 | 6/1972 | Frank | 73/864.82 |
| 3,967,505 | 7/1976 | Feichtinger | 73/DIG. 9 |
| 4,226,119 | 10/1980 | Buser | 73/864.82 |

*Primary Examiner*—S. Clement Swisher
*Attorney, Agent, or Firm*—Price, Heneveld, Huizenga & Cooper

[57] ABSTRACT

The sampling tube of the present invention is cost effective in its design and operates efficiently and relatively quickly in order to obtain a complete hydrogen sample although its application is not necessarily limited to the sampling of hydrogen content of a molten specimen.

A sampling tube includes a pair of concentric tubes with an inner tube projecting outwardly and having a fusible end cap at an extending end which, when submerged in a molten sample, admits the molten sample into the evacuated tube. The inner tube has a substantially uniform cross-sectional diameter to freely allow the molten sample to fill the inner tube and solidify as the tube is removed. Diffusible hydrogen flows from the inner tube into the outer tube through a flow-reversing cap and passageway at the opposite end of the inner tube. The tube piercing apparatus includes a clamp into which the sampling tube is placed for holding the tube in position and automatically piercing the outer tube at spaced locations along its axis for the removal of gas samples therefrom for analysis.

20 Claims, 10 Drawing Figures

SAMPLING TUBE AND APPARATUS

BACKGROUND OF THE INVENTION

The present invention relates to a sampling tube for obtaining molten metal samples and apparatus for use in removing specimen gas from the resultant sample.

In the determination of the content of molten metal, such as during a steel manufacturing process, it is desirable to monitor the content of the melt during various stages of production. A variety of sampling devices have been suggested, particularly for use with specimen gases such as hydrogen, which is particularly difficult to sample and determine inasmuch as gaseous hydrogen can easily escape while residual hydrogen remains in the solid specimen removed by the sampling device. U.S. Pat. No. 3,967,505 discloses one sampling structure for the removal of a sample from a molten metal in an effort to capture the total hydrogen content of a sample. The structure disclosed provides a pair of evacuated chambers divided into upper and lower sections by a porous plug and which includes a restricted entryway such that as the sample is removed it solidifies to seal the sampling tube. The construction of the sampling device disclosed in this patent is somewhat complicated and expensive involving several interfitted parts.

SUMMARY OF THE PRESENT INVENTION

The sampling tube of the present invention is cost effective in its design and operates efficiently and relatively quickly in order to obtain a complete hydrogen sample although its application is not necessarily limited to the sampling of a hydrogen content of a molten specimen.

The system of the present invention provides a sampling tube including a pair of concentric tubes with an inner tube projecting outwardly and having a fusible end cap at an extending end which, when submerged in a molten sample, admits the molten sample into the evacuated tube. The inner tube has a substantially uniform cross-sectional diameter to freely allow the molten sample to fill the inner tube and solidify as the tube is removed. Diffusible hydrogen flows from the inner tube into the outer tube through a flow-reversing cap and passageway at the opposite end of the inner tube.

The present invention includes an apparatus into which the sampling tube can manually be placed for holding the tube in position and automatically piercing the outer tube at spaced locations along its axis for the removal of gas samples therefrom for analysis. Once the diffusible hydrogen has been removed and analyzed, the tube can be broken or cut to provide access to the solid sample obtained within the inner tube for subsequent analysis of residual hydrogen.

These and other features, advantages and objects of the present invention will become apparent to those skilled in the art upon reading the following description thereof together with reference to the drawing figures in which:

DETAILED DESCRIPTION OF THE PREFERRED EMBODIMENT

Figure 1:
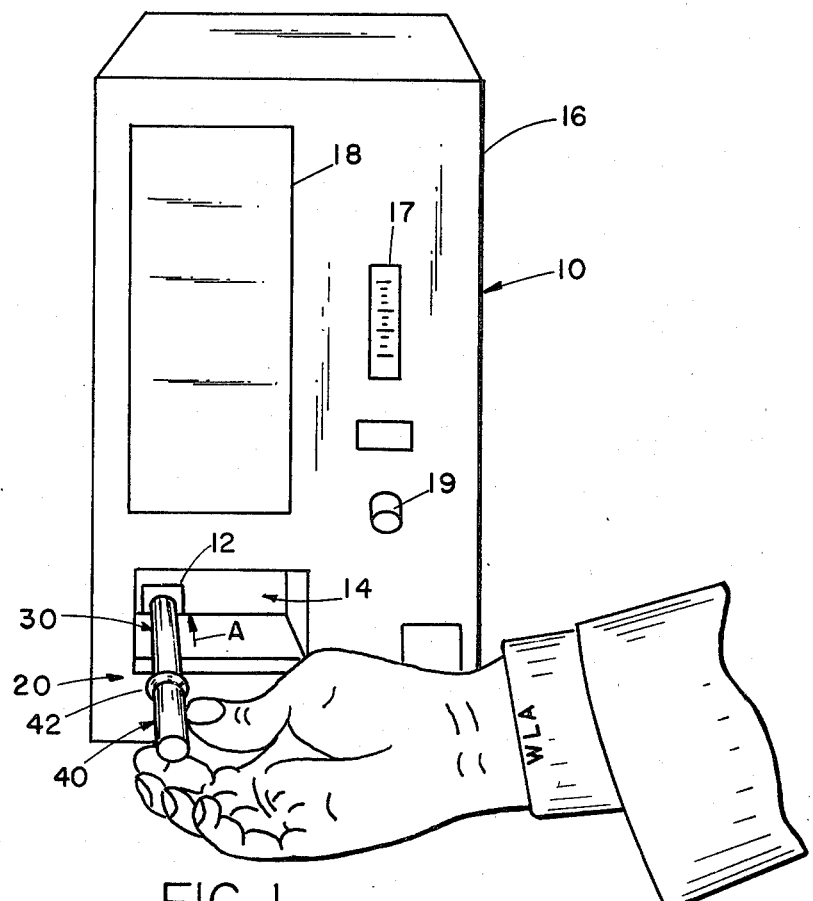
FIG. 1 is a perspective view of the apparatus and the sampling tube illustrating the use of such apparatus.
Figure 4:
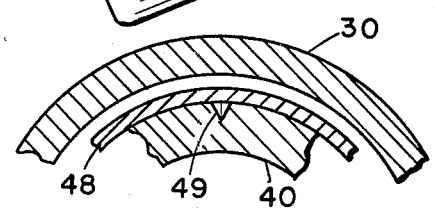
FIG. 4 is an enlarged, fragmentary, cross-sectional view of a portion of the structure shown in FIG. 2 taken along section line IV—IV of FIG. 2.
Figure 2:
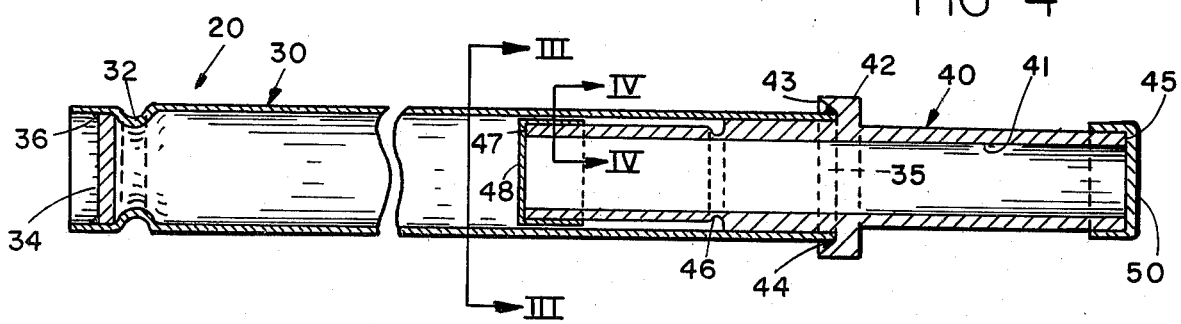
FIG. 2 is an enlarged, vertical cross-sectional view of the sampling tube embodying the present invention.
Figure 3:
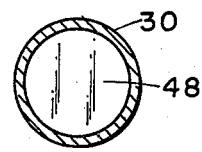
FIG. 3 is a cross-sectional view taken along section line III—III of FIG. 2.

Referring initially to FIG. 1, there is shown an apparatus 10 for the automatic piercing of a generally cylindrical sampling tube 20 which is manually inserted within an opening 12 in the rear wall of a recess 14 of apparatus 10, as illustrated by the direction indicated by arrow A in FIG. 1. Apparatus 10 which is described in greater detail below, includes a cabinet 16 having a decorative face plate 18 including instructional and identificational information, a gas flow meter 17 and an on/off switch 19. The apparatus automatically pierces the sampling tube 20 once inserted into aperture 12 to provide a flow path therethrough to remove diffusible hydrogen captured within the sampling tube during one stage of the analysis of a sample. The sampling tube is shown in detail in FIGS. 2 through 4 which are now described.

Sampling tube 20 includes a circular-cylindrical outer tube 30 and partially coaxially mounted therein a cylindrical inner or sampling tube 40. The steel outer tube has an overall length, in the preferred embodiment, of approximately 4.75 inches, an outer diameter of approximately 0.5 inches and an inner diameter of approximately 0.46 inches. Near one end of tube 30 there is an annular roll-formed depression 32 defining a stop for a disc-shaped end cap 34 inserted in the end and brazed around its periphery, as indicated by bead 36, to sealably enclose this end of tube 30 during the manufacturing process. The opposite end 35 of tube 30 is initially open to receive coaxially fitted inner tube 40. Steel tube 40 is also circular-cylindrical, and it has an overall length of approximately 2.25 inches with an annular collar 42 formed inwardly from an extending first end 45 a distance of approximately 1 inch. Collar 42 has a rearward facing tapered annular recess 43 therein defining a seat for the end 35 of tube 30 which junction is sealed by a brazing bead 44 during assembly. Inner tube 40 includes an annular recess 46 formed approximately ½ inch behind collar 42 to define a breaking point for snapping off the end of tube 40 remote from end 45 which contains a solid sample after use. The first end 45 of tube 40 includes a fusible end cap 50 brazed thereon and made of stainless steel having a thickness of 0.006 inches which melts when the sample is immersed in a molten metal bath. At the opposite end of tube 40 there is provided a gas flow reversal closure cap 48 with a cylindrical flange which is press-fit over the end 47 of tube 40 and cooperatively defines a gas flow path or passageway parallel to the longitudinal axes of tubes 30 and 40 and which, in the preferred embodiment of the invention, comprises at least a pair of longitudinally extending scribe indentations 49 (FIG. 4) having a length of approximately 0.5 inches and formed in the outer peripheral wall of tube 40 under the flange of cap 48. The scribe marks 49 have a depth of approximately 0.020 inches and a pair of 180° spaced scribed marks were provided in the preferred embodiment of the invention. Tubes 30 and 40 are made of suitable material such as steel with the inner tube defining a smooth cylindrical uniform diameter surface 41 having a diameter of approximately 0.258 inches extending along its length. The outer diameter of tube 40 and cap 48 is slightly less than the inner diameter of tube 30 to permit ready assembly of the two tubes during manufacturing.

During assembly, cap 48 is first fitted over the scribed end of tube 40, cap 50 fitted over end 45 of tube 40 and the tubes physically positioned together. Cap 34 is then positioned on stop 32. The structure is then placed in a suitable vacuum chamber to evacuate the tube to approximately $10^{-4}$ millimeters and caps 34 and 50 and collar 42 braced in place. Thus, the assembly is evacuated during manufacturing to provide a negative pressure sealed unit. Tube 20 is then conventionally inserted into a cardboard sleeve and partially surrounded by an insulating material with end 45 exposed a distance of approximately 0.625 inches for immersion into a metal bath for the withdrawing of a molten metal sample. As the sample is taken, cap 50 melts allowing the admission of the molten metal into tube 40 along uniform cylindrical passageway 41 until it strikes cap 48 after some cooling which effectively stops the flow and tends to reverse the flow of direction of molten metal which is effectively prevented thereby. Diffusible hydrogen contained in the molten metal reverses its direction and flows in the direction toward sealed collar 42, through passageways 49, through the annular space between tubes 30 and 40, and into the volume defined by the inner cylindrical space of outer tube 30 and is contained therein. Some of the diffusible hydrogen diffuses through the sample form wall as well. The molten sample solidifies as the sampling tube is removed from the melt to seal the end 45 of cylindrical bore 40 to effectively trap the diffusible hydrogen within tube 30 and the solid metal sample within tube 40.

Figure 5:
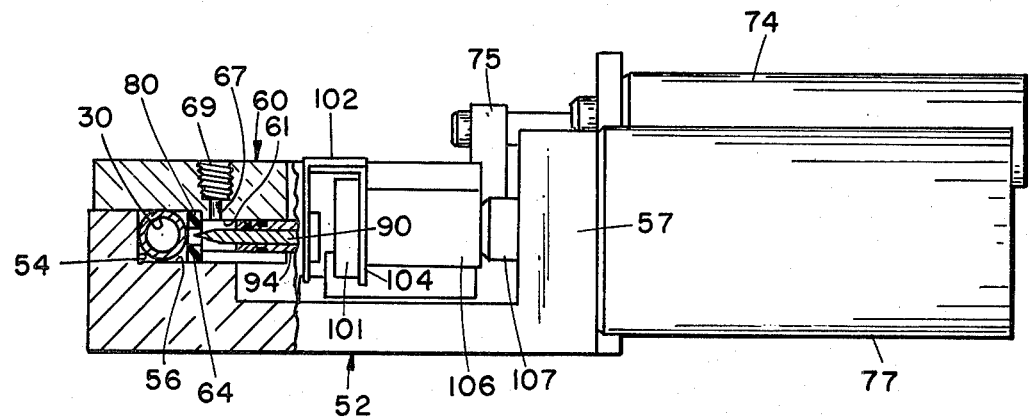
FIG. 5 is a fragmentary, cross-sectional view, partly broken away, of one piercing section of the apparatus shown in FIG. 1 shown in a first operational position.
Figure 6:
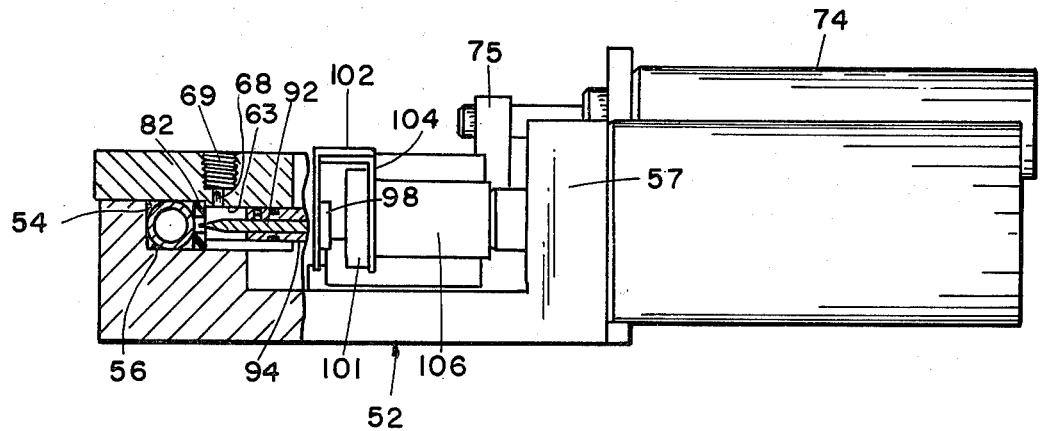
FIG. 6 is a fragmentary, cross-sectional view, partly broken away, of another piercing section of the apparatus shown in FIG. 1 shown in a second operational position.
Figure 7:
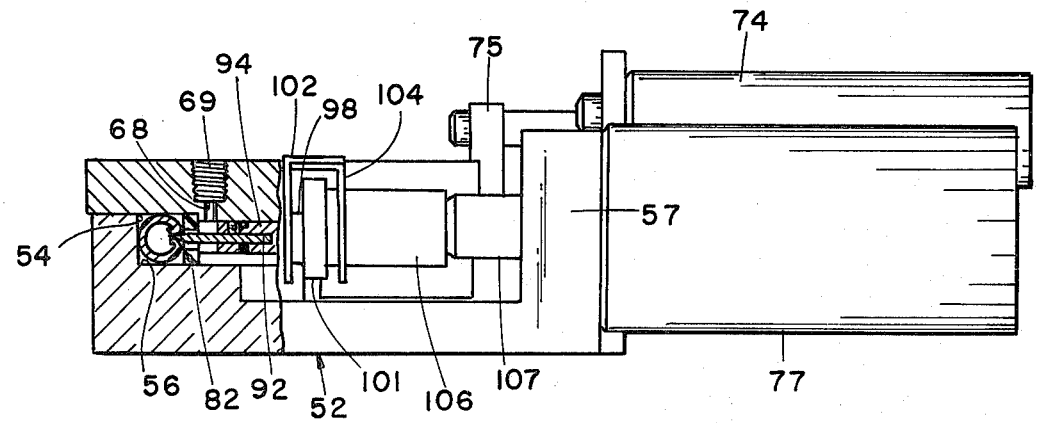
FIG. 7 is a fragmentary, cross-sectional view, partly broken away, of the portion of the apparatus shown in FIGS. 1 and 6 shown in a third operational position.

In order to remove the diffusible or free hydrogen from sampling tube 20, for analysis, the automatic sampling tube piercing apparatus, shown in FIGS. 1 and 5 through 10 is employed with initial reference to FIGS. 5 through 7 pertaining to the description of the operative portion of the sampling tube clamping and piercing mechanism contained within apparatus 10.

Figure 8:
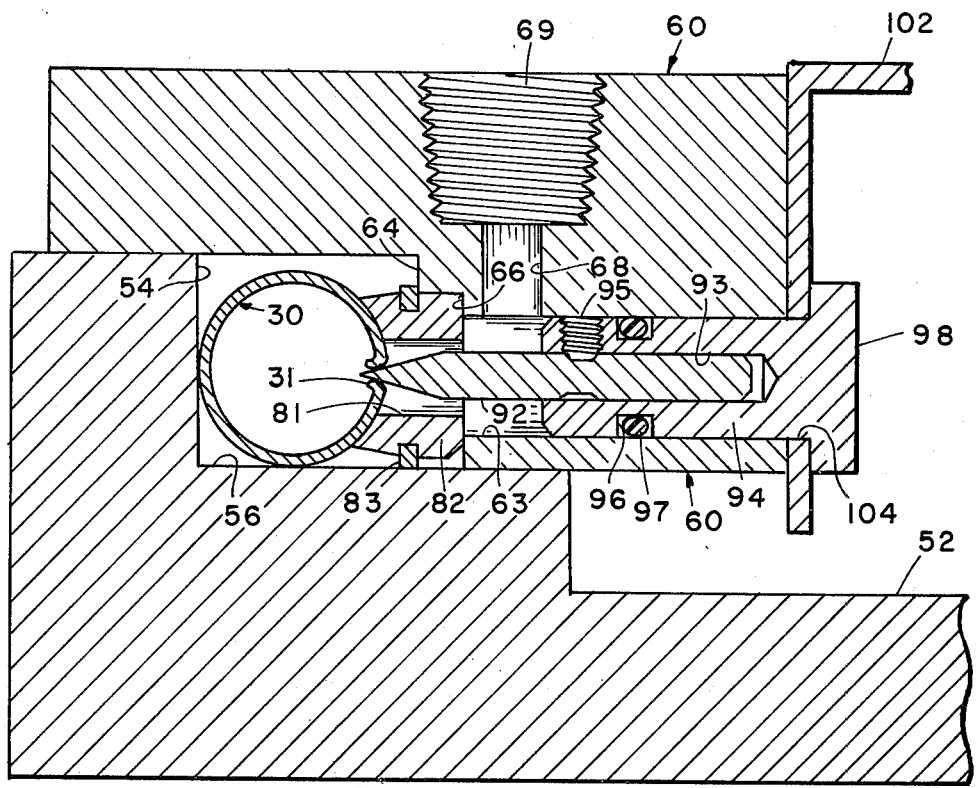
FIG. 8 is an enlarged, fragmentary, cross-sectional view of a portion of the structure shown in FIG. 7.

The sampling tube piercing apparatus includes a generally U-shaped base 52, as viewed from the side (FIGS. 5 through 7), having an end ledge defining a vertically extending wall 54 and floor 56 against which the sampling tube 30 is held by an inverted L-shaped slide (side elevation) 60. Walls 54 and 56 lie in alignment and adjacent to opening 12 in cabinet 16 (FIG. 1) such that as the sampling tube is inserted, it will rest on floor 56 between side wall 54 and an opposing side wall 64 of slide 60. Slide 60 moves on base 52 between an open position retracted to the right, as seen in FIG. 5, to a clamped position, as seen in FIGS. 6, 7 and 8, and includes a pair of horizontally extending cylindrical apertures 61 and 63 (FIGS. 5 and 6, respectively) horizontally spaced from one another and extending transverse to the longitudinal axis of tube 30 in spaced relationship to extend adjacent opposite ends of the open portion of tube 30. The spacing, in the preferred embodiment, of apertures 61 and the piercing needles concentrically mounted therein, as described below, is approximately 2.75 inches from center-to-center. Base 52 also includes an end wall, opposite opening 12 in which there is mounted a limit switch 65 (FIG. 9) such that insertion of the sampling tube fully between the base and slide in aperture 12 will activate switch 65 to initiate a cycle of operation.

Figure 9:
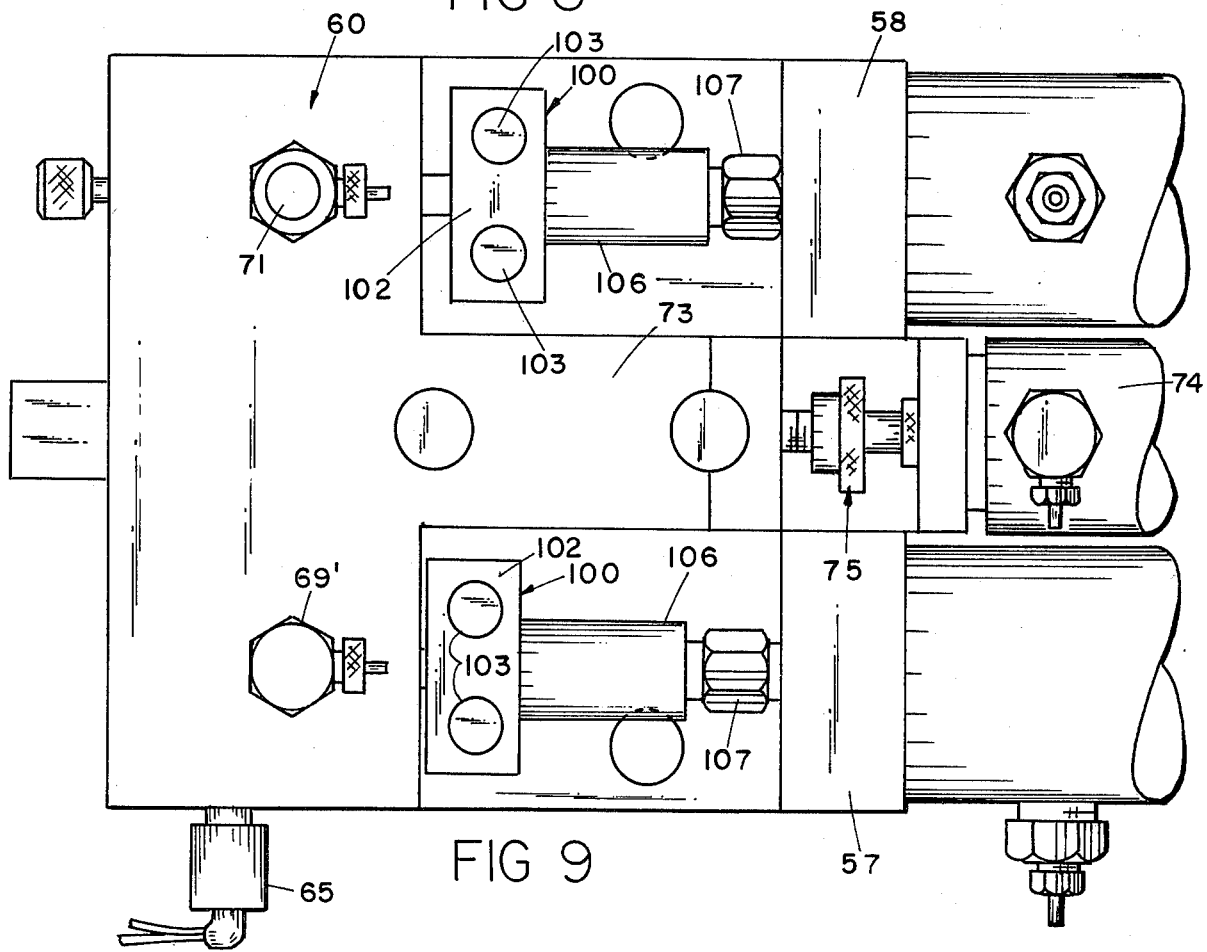
FIG. 9 is an enlarged, fragmentary, top plan view of the structure shown in FIGS. 5 through 7.

Base 52 also integrally includes a pair of spaced vertically extending mounting bosses 57 and 58 for mounting thereon needle activating cylinders 77 and 78, respectively. Slide 60 is generally T-shaped in plan view (FIG. 9) including a center leg 73 which is secured to the shaft of a slide activating double acting pneumatic cylinder 74 by an adjustable coupling 75, as best seen in FIG. 9. Mounted in concentric relationship with apertures 61 and 63 against and within annular recesses 66 in opposing wall 64 are a pair of spaced rubber grommet-shaped seals 80 and 82 for surrounding the piercing area of sampling tube 30 to form a seal therearound during the clamping, piercing and hydrogen removal phases of operation. The seals are secured to wall 64 by means of a metal seal holding plate 83 (FIG. 8) having apertures formed therein, the border of which fits within the annular groove in the grommet-shaped seals 80 and 82. Each of the seals 80 and 82 include a central opening 81 (FIG. 8) which are aligned with apertures 61 and 63 in the seal holding slide. Apertures 61 and 63 in turn communicate with vertical gas flow passageways 67 and 68 which in turn communicate with threaded apertures 69 for receiving gas line fittings 69' and 71 (FIG. 9) which provide a gas flow path for carrier gas and removed hydrogen, as described in connection with FIG. 10.

The needle puncturing mechanism includes a pair of tool steel tapered needles 90 and 92 secured to a pair of needle carriers 94, one of which is best seen in FIG. 8, and each of which includes a central recess 93 for receiving the end of each of the needles remote from the tip 91. Each needle is secured within aperture 93 by means of a set screw 95 and behind which there is provided an annular groove 96 for receiving an O-ring seal 97 to seal the end of passageways 61 and 63 remote from the sampling tube 30. Thus, the interior space of tube 30 will, when punctured, communicate with each of the sealed passageways 61 and 63 through grommets 80 and 82 and the apertures 67 and 68 to the fittings 69' and 71.

Each of the needle carriers is coupled to a generally U-shaped, adjustable coupling 100 which has a forward L-shaped leg 102 with an aperture 104 (FIG. 8) therein which loosely fits around an enlarged head 98 of needle carriers 94. Each coupling 100 also includes a second L-shaped leg 104 secured to the first leg 102 by fastening screws 103 (FIG. 8) with leg 104 in turn loosely fitted behind the head 101 of a needle driving ram 106 (FIGS. 5 through 7 and 9) coupled to cylinders 77 and 78 for the respective needles by threaded coupling 107.

The construction of coupling 100 thereby allows relative ease of assembly of the needle carriers within the clamp slide and coupling of the slide and needle carriers to the respective activating cylinders. Some play is provided, as can be seen in FIGS. 6 and 7, where in FIG. 6 the needle piercing cylinders are in a retracted position with the rams 106 being spaced from the ends 98 of the needle carriers while in FIG. 7, in the piercing position, the cylinders are activated, forcing the heads 101 of rams 106 against the needle carriers, sliding them longitudinally in a direction toward the sampling tube 30 within the bores 61 and 63 of the slide, as best seen in FIG. 7. A cycle of operation of the sampling tube piercing apparatus can best be understood with reference to FIG. 10 which shows the flow path of gas through the system and the electrically operated valve controlling elements therefor.

Figure 10:
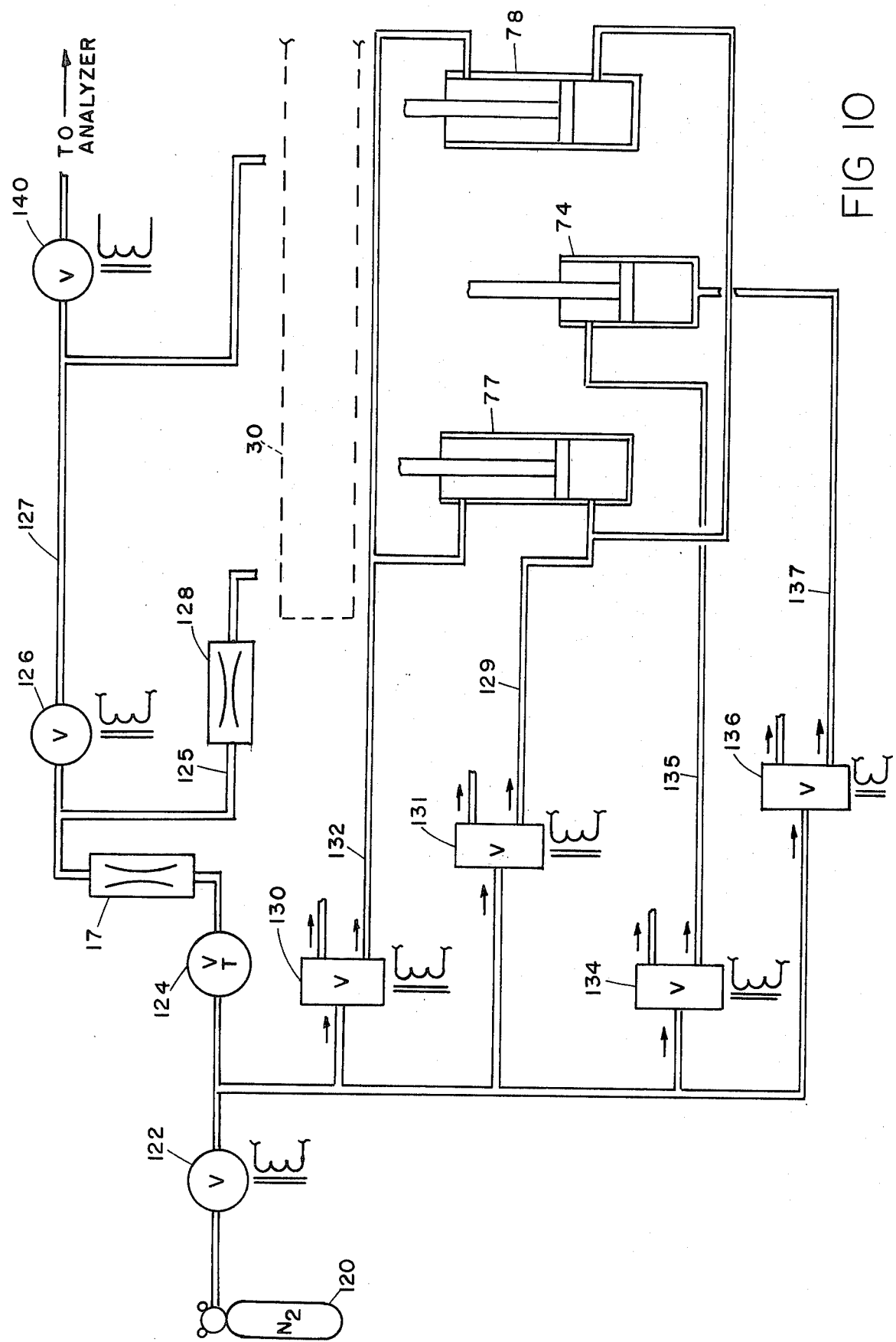
FIG. 10 is a schematic diagram of the gas flow path and control system of the apparatus shown in FIG. 1.

As the sampling tube with captured diffusible hydrogen is inserted in aperture 12 of the sample piercing apparatus 10, its end 34 will engage the limit switch 65 (FIG. 9) and begin an automatic sequence of operation of a series of valves, shown in the flow diagram of FIG. 10. Carrier gas such as nitrogen is supplied at about 40 p.s.i. from a tank 120 upon actuation of switch 65. Actuation of switch 65 begins a sequence of automatic operation beginning with the actuation of valve 122 to an open position permitting the carrier gas to flow through a first flow controller 124 which limits the flow of gas to approximately 0.1 liters per minute. The flow of gas then proceeds through a flow meter 17 (also shown in FIG. 1) to a branch including a normally closed valve 126 and an adjustable needle valve 128 to the inlet side of the piercing device corresponding to the enclosed end 34 of tube 30 through fitting 69', shown in FIG. 9. A cylinder controlling valve 130 is normally in an open position permitting gas pressure in conduit 132 to retract piercing cylinders 77 and 78. Also, initially, a normally open valve 134 applys the 40 p.s.i. pressure through conduit 135 to retract the clamping cylinder 74. Of the 0.1 liters per minute of flow through flow meter 17, approximately 90% of the flow passes through a normally open valve 126 and conduit 127 and is blocked by a normally closed valve 140 to purge conduit 127 extending to the piercing needle carrier fitting 71 (FIG. 9) while 10% of the 0.1 liter per minute flow passes through conduit 125 and through needle valve 128 to fitting 69'. Thus, prior to piercing of the sampling tube, conduits 125 and 127 are being continuously purged by the N₂ carrier gas. After a predetermined purge time set by a conventional timing circuit, valves 134 and 136 are cycled to relieve pressure on conduit 135, holding the clamping cylinder 74 in a retracted position and opening valve 136 to cause clamp cylinder 74 to activate slide 60, thereby clamping the sampling tube in position. Thus, by activation of valve 136, the 40 p.s.i. pressure is applied to conduit 137 coupled to the cylinder 74, as represented schematically in FIG. 10, to clamp the sampling tube in place with seals 80 and 82 (FIGS. 5 through 8) sealably surrounding the piercing area of the wall of sampling tube 30.

After this clamping of the sampling tube in place, valves 130 and 131 are also cycled with valve 130 closing and venting conduit 132 to atmosphere and valve 131 opening to apply pressure to conduit 129 coupled to cylinders 77 and 78 to move piercing needles 90 and 92 into engagement and through the cylindrical wall of the outer sampling tube 30. The needle movement is approximately 0.070 inches to provide a pair of spaced holes 31 (FIG. 8) each of approximately 3/32 of an inch diameter through the wall of the tube. The piercing movement of the needles is shown in FIGS. 7 and 8. After approximately 2 seconds, to provide sufficient time for the piercing needles to fully penetrate the outer tube 30, valves 130 and 131 are again cycled to retract the piercing needles. Valve 126 is then activated to close and valve 140 opened, forcing the flow path of carrier gas through conduit 125, the gas passageways in slide 60 including conduits 66, 68 and 61 and 67, through tube 30 and conduit 127 out through valve 140 to an analyzer (not shown). This carries the diffusible hydrogen into the hydrogen analyzer for analysis.

Once analysis is complete, which can be indicated by a control signal from the analyzer to the control circuit for the piercing apparatus, valves 126 and 140 are cycled to their open and closed positions, respectively, and valves 134 and 136 cycled to unclamp the sampling tube. This permits it to be removed from the piercing apparatus for subsequent cutting of the solid sample from inner tube 30 along scribe line 46 (FIG. 2) to provide a pin sample for analysis by a conventional hot extraction process in which the solid pin sample is heated to approximately 1200° C. and the hydrogen driven off and subsequently analyzed to provide the total hydrogen content of a molten metal sample. The specific analyzer and control circuit for cycling the valves as described above can be conventional.

It will be apparent to those skilled in the art that various modifications to the preferred embodiment of the present invention can be made without departing from the spirit or scope thereof as defined by the appended claims.

The embodiments of the invention in which an exclusive property or privilege is claimed are defined as follows:

1. A molten metal sampling device comprising:
    an outer cylindrical tube sealably enclosed at one end and open at an opposite end; and
    a cylindrical sampling tube coaxially and sealably fitted at least partially within said opposite end of said outer tube and having an extending end sealed with a fusible material and an opposite end positioned within said outer tube and including closure means for blocking the flow of molten metal into said outer tube while permitting reverse direction flow of gases therein, and wherein the interior of said outer and sampling tube is evacuated to a negative pressure.

2. The apparatus as defined in claim 1 wherein said closure means includes an end cap with flange means extending axially over said opposite end of said sampling tube.

3. The apparatus as defined in claim 2 wherein said closure means includes passageway means extending between said flange means and the outer surface of said opposite end of said sampling tube.

4. The apparatus as defined in claim 3 wherein said passageway means comprises at least one axially extending channel formed in said outer surface of said sampling tube.

5. The apparatus as defined in claim 4 wherein said passageway means comprises a pair of opposed scribe lines having a depth of about 0.020 inches.

6. A molten metal sampling device comprising:
    an outer cylindrical tube sealably enclosed at one end and open at an opposite end; and
    a cylindrical sampling tube having a uniform diameter cylindrical inner wall and coaxially and sealably fitted at least partially within said opposite end of said outer tube and having an extending end sealed with a fusible material and an opposite end positioned within said outer tube and including closure means for blocking the flow of molten metal into said outer tube while permitting the flow of gas into the interior of said outer tube, and wherein the interior of said outer and sampling tube is evacuated to a negative pressure.

7. The apparatus as defined in claim 6 wherein said closure means permits the flow of gas in a direction toward said extending end and includes an end cap with flange means extending axially over said opposite end of said sampling tube.

8. The apparatus as defined in claim 7 wherein said closure means includes passageway means extending between said flange means and the outer surface of said opposite end of said sampling tube.

9. The apparatus as defined in claim 8 wherein said passageway means comprises at least one axially extending channel formed in said outer surface of said sampling tube.

10. The apparatus as defined in claim 9 wherein said passageway means comprises a pair of opposed scribe lines having a depth of about 0.020 inches.

11. Apparatus for piercing a molten metal sampling tube comprising:
a base;
slide means movably positioned on said base to define a tube receiving opening, said slide means including a pair of spaced annular seals positioned on said slide for sealably engaging the wall of a sampling tube;
means for moving said slide between an open tube receiving position and a tube clamping position in which said seals sealably engage a sampling tube;
a pair of piercing members movably supported by said slide and positioned in concentric alignment with said seals; and
means for moving said piercing members between an extended position to pierce apertures in the wall of a tube and a retracted position to expose the apertures.

12. The apparatus as defined in claim 11 and further including means defining a gas inlet passageway communicating with the annular space of one seal and a gas outlet passageway communicating with the annular space of the other seal.

13. The apparatus as defined in claim 12 wherein each of said piercing members includes a cylindrical needle holding member sealably and slidably mounted to said slide and having a piercing needle mounted thereto.

14. The apparatus as defined in claim 13 wherein said means for moving said slide includes cylinder means extending between said base and said slide.

15. The apparatus as defined in claim 14 wherein said means for moving each of said piercing members comprises a piercing cylinder extending between said base and said needle holding member.

16. Apparatus for extracting specimen gas from a sealed molten metal sampling tube comprising:
a base;
slide means movably positioned on said base to define a tube receiving opening, said slide means including seal means for sealably engaging the wall of a sampling tube;
means for moving said slide between a tube receiving position and a tube clamping position in which said seal means sealably engages a sampling tube;
means for piercing the wall of a sampling tube supported by said slide; and
means defining gas inlet and gas outlet passageways communicating with a tube held by said slide to provide a gas flow path through the tube.

17. The apparatus as defined in claim 16 and further including a sampling tube comprising:
an outer cylindrical tube sealably enclosed at one end and open at an opposite end; and
a cylindrical sampling tube coaxially and sealably fitted at least partially within said opposite end of said outer tube and having an extending end sealed with a fusible material and an opposite end positioned within said outer tube and including closure means for blocking the flow of molten metal into said outer tube while permitting reverse direction flow of gases therein, and wherein the interior of said outer and sampling tube is evacuated to a negative pressure.

18. Apparatus for piercing a molten metal sampling tube comprising:
means for receiving a sampling tube;
clamp means including seal means for sealably engaging the wall of a sampling tube;
means for moving said clamp means between a tube receiving position and a tube clamping position in which said seal means sealably engages a sampling tube;
means for piercing apertures in a sampling tube at spaced locations; and
means defining gas inlet and gas outlet passageways communicating with the apertures formed in a tube held by said clamp means to provide a gas flow path through the tube.

19. The apparatus as defined in claim 18 wherein said seal means comprises a pair of spaced seals and wherein said piercing means comprises a pair of piercing members aligned with said seals.

20. The apparatus as defined in claim 19 wherein said clamp means includes a base, a slide movably positioned on said base and cylinder means extending between said base and slide for moving said slide between tube receiving and tube clamping positions.

* * * * *